United States Patent
Johnson et al.

(10) Patent No.: US 7,439,243 B2
(45) Date of Patent: Oct. 21, 2008

(54) PIPERAZINYL-QUINOLINE DERIVATIVES USEFUL FOR THE TREATMENT OF CNS DISORDERS

(75) Inventors: Christopher Norbert Johnson, Harlow (GB); Stephen Frederick Moss, Harlow (GB); David R Witty, Harlow (GB)

(73) Assignee: Glaxo Group Limited, Greenford, Middlesex (GB)

( * ) Notice: Subject to any disclaimer, the term of this patent is extended or adjusted under 35 U.S.C. 154(b) by 238 days.

(21) Appl. No.: 10/572,671

(22) PCT Filed: Sep. 23, 2004

(86) PCT No.: PCT/EP2004/010845

§ 371 (c)(1),
(2), (4) Date: Mar. 20, 2006

(87) PCT Pub. No.: WO2005/030724

PCT Pub. Date: Apr. 7, 2005

(65) Prior Publication Data
US 2007/0027139 A1 Feb. 1, 2007

(30) Foreign Application Priority Data
Sep. 25, 2003 (GB) .................................. 0322510.9

(51) Int. Cl.
*A61K 31/496* (2006.01)
*A61K 31/551* (2006.01)
*C07D 215/40* (2006.01)

(52) U.S. Cl. ............ 514/253.06; 514/218; 514/253.07; 540/575; 544/363

(58) Field of Classification Search ....................... None
See application file for complete search history.

(56) References Cited

U.S. PATENT DOCUMENTS

| 6,313,126 B1 | 11/2001 | Meagher et al. ............. 514/249 |
| 2003/0013708 A1 | 1/2003 | Haeberlein et al. ....... 514/231.5 |
| 2004/0024210 A1 * | 2/2004 | Johansson et al. ........... 544/183 |

FOREIGN PATENT DOCUMENTS

WO WO 03/035061 A1 5/2003
WO WO 03/080580 A2 10/2003

OTHER PUBLICATIONS

Robichaud et al. in Annual Reports in Medicinal Chemistry, vol. 36, p. 11-20 (2000).*
Rogers et al. Psychopharmacology, vol. 158, p. 114-119 (2001).*
Bromidge et al. Bioorganic & Medicinal Chemistry Letters, vol. 11, p. 55-58 (2001).*
Ahmed et al. Bioorganic & Medicinal Chemistry Letters vol. 15, p. 4867-4871 (2005).*
Heal et al. Pharmacology & Therapeutics, vol. 117, p. 207-231 (2008).*
Woolley et al. *Neuropharmacology*, vol. 41: 210-219 (2001).
Mitchell et al., *Pharmacol. & Therapeutics*, 108: 320-333 (2005).
Chuang et al., *Alzheimer's & Dementia, The Journal of the Alzheimer's Association*, 2(3/Supp. 1): S631-S632 (2006).
London Stock Exchange Announcement—GlaxoSmithKline (GSK) plc, Issued on Thursday, Dec. 13, 2007, New York, New York.
A Dose Ranging Study to Investigate the Efficacy and Safety of SB-742457 in Alzheimer's Disease. NCT ID No. NCT00224497 (Verified 2007).
SB-742457 and Donepezil in Alzheimer's Disease. NCT ID No. NCT00348192 (2006).
Garcia-Alloza et al. *Neuropsychopharmacology*, 29: 410-416 (2004).

* cited by examiner

*Primary Examiner*—Emily Bernhardt
(74) *Attorney, Agent, or Firm*—Kathryn L. Sieburth; Mary E. McCarthy; Charles M. Kinzig

(57) ABSTRACT

Disclosed are quinoline compounds of formula (I) having pharmacological activity, processes for their preparation, compositions containing them, and methods for the treatment of CNS and other disorders.

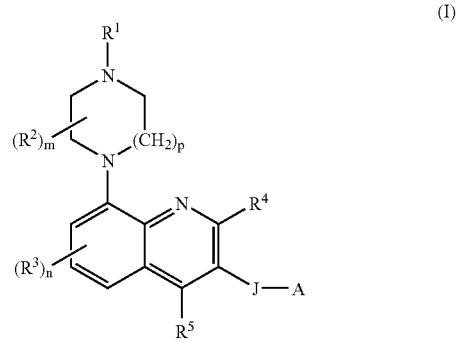

12 Claims, No Drawings

PIPERAZINYL-QUINOLINE DERIVATIVES USEFUL FOR THE TREATMENT OF CNS DISORDERS

This invention relates to novel quinoline compounds having pharmacological activity, to processes for their preparation, to compositions containing them and to their use in the treatment of CNS and other disorders.

JP 02262627 (Japan Synthetic Rubber Co) describes a series of substituted quinoline derivatives useful as wavelength converting elements. WO 00/42026 (Novo Nordisk) describes a series of quinoline and quinoxaline compounds for use as GLP-1 agonists.

A structurally novel class of compounds has now been found which also possess affinity for the 5-HT$_6$ receptor. The present invention therefore provides, in a first aspect, a compound of formula (I) or a pharmaceutically acceptable salt thereof:

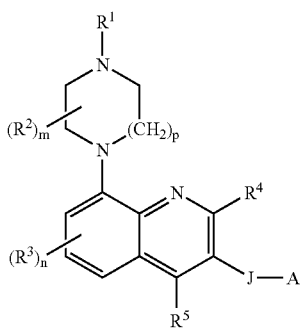

(I)

wherein:
R$^1$ represents hydrogen, —C$_{1-6}$ alkyl, —C$_{0-4}$ alkyl-C$_{3-8}$cycloalkyl, —C$_{2-4}$ alkoxy-C$_{1-4}$ alkyl, —C$_{1-4}$ alkyl-aryl, —C$_{1-4}$ alkyl-heteroaryl or —C$_{0-4}$ alkyl-heterocyclyl, or R$^1$ is linked to R$^2$ to form a group (CH$_2$)$_2$, (CH$_2$)$_3$ or (CH$_2$)$_4$; wherein said alkyl, cycloalkyl, aryl, heteroaryl or heterocyclyl groups of R$^1$ may be optionally substituted by one or more (e.g. 1, 2 or 3) halogen, C$_{1-6}$ alkyl, C$_{1-6}$ alkoxy, cyano, amino or trifluoromethyl groups;
R$^2$ represents hydrogen or C$_{1-6}$ alkyl;
m represents an integer from 1 to 4, such that when m is an integer greater than 1, two R$^2$ groups may instead be linked to form a CH$_2$, (CH$_2$)$_2$ or (CH$_2$)$_3$ group;
R$^3$, R$^4$ and R$^5$ independently represent hydrogen, halogen, cyano, —CF$_3$, —CF$_3$O, C$_{1-6}$ alkyl, C$_{1-6}$ alkoxy, C$_{1-6}$ alkanoyl or a group —CONR$^6$R$^7$;
R$^6$ and R$^7$ independently represent hydrogen or C$_{1-6}$ alkyl or R$^6$ and R$^7$ together with the nitrogen to which they are attached may form a nitrogen containing heterocyclyl or heteroaryl group;
n represents an integer from 1 to 3;
p represents 1 or 2;
J represents CH$_2$, CO, CF$_2$, CH(OR$^8$), NR$^9$, SO, O or S;
R$^8$ and R$^9$ independently represent hydrogen or C$_{1-6}$ alkyl;
A represents an -aryl, -heteroaryl, -aryl-aryl, -aryl-heteroaryl, -heteroaryl-aryl or -heteroaryl-heteroaryl group;
wherein said aryl and heteroaryl groups of A may be optionally substituted by one or more (e.g. 1, 2 or 3) substituents which may be the same or different, and which are selected from the group consisting of halogen, hydroxy, cyano, nitro, trifluoromethyl, trifluoromethoxy, C$_{1-6}$ alkyl, trifluoromethanesulfonyloxy, pentafluoroethyl, C$_{1-6}$ alkoxy, arylC$_{1-6}$ alkoxy, C$_{1-6}$ alkylthio, C$_{1-6}$ alkoxyC$_{1-6}$ alkyl, C$_{3-7}$ cycloalkylC$_{1-6}$ alkoxy, C$_{1-6}$ alkanoyl, C$_{1-6}$ alkoxycarbonyl, C$_{1-6}$ alkylsulfonyl, C$_{1-6}$ alkylsulfinyl, C$_{1-6}$ alkylsulfonyloxy, C$_{1-6}$ alkylsulfonylC$_{1-6}$ alkyl, arylsulfonyl, arylsulfonyloxy, arylsulfonylC$_{1-6}$ alkyl, C$_{1-6}$ alkylsulfonamido, C$_{1-6}$ alkylamido, C$_{1-6}$ alkylsulfonamidoC$_{1-6}$ alkyl, C$_{1-6}$ alkylamidoC$_{1-6}$ alkyl, arylsulfonamido, arylcarboxamido, arylsulfonamidoC$_{1-6}$ alkyl, arylcarboxamidoC$_{1-6}$ alkyl, aroyl, aroylC$_{1-6}$ alkyl, arylC$_{1-6}$ alkanoyl, or a group CONR$^{10}$R$^{11}$ or SO$_2$NR$^{10}$R$^{11}$, wherein R$^{10}$ and R$^{11}$ independently represent hydrogen or C$_{1-6}$ alkyl or R$^{10}$ and R$^{11}$ together with the nitrogen atom to which they are attached may form a nitrogen containing heterocyclyl or heteroaryl group;

or solvates thereof.

Alkyl groups, whether alone or as part of another group, may be straight chain or branched and the groups alkoxy and alkanoyl shall be interpreted similarly. Alkyl moieties are more preferably C$_{1-4}$ alkyl, e.g. methyl or ethyl. The term 'halogen' is used herein to describe, unless otherwise stated, a group selected from fluorine, chlorine, bromine or iodine.

The term "aryl" includes single and fused rings for example, phenyl or naphthyl.

The term "heteroaryl" is intended to mean a 5-7 membered monocyclic aromatic or a fused 8-10 membered bicyclic aromatic ring containing 1 to 3 heteroatoms selected from oxygen, nitrogen and sulfur. Suitable examples of such monocyclic aromatic rings include thienyl, furyl, pyrrolyl, triazolyl, imidazolyl, oxazolyl, thiazolyl, oxadiazolyl, isothiazolyl, isoxazolyl, thiadiazolyl, pyrazolyl, pyrimidyl, pyridazinyl, pyrazinyl and pyridyl. Suitable examples of such fused aromatic rings include benzofused aromatic rings such as quinolinyl, isoquinolinyl, quinazolinyl, quinoxalinyl, cinnolinyl, naphthyridinyl, indolyl, indazolyl, pyrrolopyridinyl, benzofuranyl, benzothienyl, benzimidazolyl, benzoxazolyl, benzisoxazolyl, benzothiazolyl, benzisothiazolyl, benzoxadiazolyl, benzothiadiazolyl and the like. Heteroaryl groups, as described above, may be linked to the remainder of the molecule via a carbon atom or, when present, a suitable nitrogen atom except where otherwise indicated above.

The term "nitrogen containing heteroaryl" is intended to represent any heteroaryl group as defined above which contains a nitrogen atom.

It will be appreciated that wherein the above mentioned aryl or heteroaryl groups have more than one substituent, said substituents may be linked to form a ring, for example a carboxyl and amine group may be linked to form an amide group.

The term "heterocyclyl" is intended to mean a 4-7 membered monocyclic saturated or partially unsaturated aliphatic ring or a 4-7 membered monocyclic saturated or partially unsaturated aliphatic ring containing 1 to 3 heteroatoms selected from oxygen or nitrogen fused to a benzene or monocyclic heteroaryl ring. Suitable examples of such monocyclic rings include pyrrolidinyl, piperidinyl, piperazinyl, morpholinyl, thiamorpholinyl, diazepanyl, azepanyl, dihydroimidazolyl, tetrahydropyranyl, tetrahydrothiapyranyl and tetrahydrofuranyl. Suitable examples of benzofused heterocyclic rings include dihydroindolyl, dihydroisoindolyl, tetrahydroquinolinyl, tetrahydrobenzazepinyl and tetrahydroisoquinolinyl.

The term "nitrogen containing heterocyclyl" is intended to represent any heterocyclyl group as defined above which contains a nitrogen atom.

Preferably, $R^1$ represents hydrogen, methyl, ethyl, isopropyl, isobutyl or 2,2-dimethylpropyl. More preferably, $R^1$ represents hydrogen or methyl, especially hydrogen.

Preferably $R^2$ represents hydrogen, methyl (e.g. 3-methyl, 2-methyl, 3,3-dimethyl or 2,5-dimethyl) or is linked to $R^1$ to form a $(CH_2)_3$ group. More preferably, $R^2$ represents hydrogen or methyl (e.g. 3-methyl), especially hydrogen.

Preferably $R^3$ represents hydrogen, methyl (e.g. 6-methyl) or halogen (e.g. 7-chloro).

More preferably, $R^3$ represents hydrogen.

Preferably $R^4$ and $R^5$ independently represent hydrogen or methyl, especially hydrogen.

Preferably n represents 1.

Preferably, m and p independently represent 1 or 2, more preferably m and p both represent 1.

In one preferred embodiment, m represents 2 and both $R^2$ groups are linked to form a $CH_2$ group linking C-2 and C-5 of the piperazine ring.

Preferably, J represents $CH_2$, O, CO, SO or S, more preferably $CH_2$, CO or O, especially $CH_2$ or CO, most especially $CH_2$.

Preferably, A represents -aryl (e.g. phenyl) optionally substituted by one or more halogen (e.g. chlorine) atoms or -heteroaryl (e.g. pyridyl), more preferably A represents -aryl (e.g. phenyl) optionally substituted by a halogen (e.g. 3-chlorine) atom, particularly 3-chlorophenyl.

Preferred compounds according to the invention include examples E1-E3 as shown below, or a pharmaceutically acceptable salt thereof.

The compounds of formula (I) can form acid addition salts thereof. It will be appreciated that for use in medicine the salts of the compounds of formula (I) should be pharmaceutically acceptable. Suitable pharmaceutically acceptable salts will be apparent to those skilled in the art and include those described in J. Pharm. Sci., 1977, 66, 1-19, such as acid addition salts formed with inorganic acids e.g. hydrochloric, hydrobromic, sulfuric, nitric or phosphoric acid; and organic acids e.g. succinic, maleic, acetic, fumaric, citric, tartaric, benzoic, p-toluenesulfonic, methanesulfonic or naphthalenesulfonic acid. The present invention includes within its scope all possible stoichiometric and non-stoichiometric forms.

The compounds of formula (I) may be prepared in crystalline or non-crystalline form, and, if crystalline, may optionally be solvated, e.g. as the hydrate. This invention includes within its scope stoichiometric solvates (e.g. hydrates) as well as compounds containing variable amounts of solvent (e.g. water).

Certain compounds of formula (I) are capable of existing in stereoisomeric forms (e.g. diastereomers and enantiomers) and the invention extends to each of these stereoisomeric forms and to mixtures thereof including racemates. The different stereoisomeric forms may be separated one from the other by the usual methods, or any given isomer may be obtained by stereospecific or asymmetric synthesis. The invention also extends to any tautomeric forms and mixtures thereof.

The present invention also provides a process for the preparation of a compound of formula (I) or a pharmaceutically acceptable salt thereof, which process comprises:

(a) reacting a compound of formula (II)

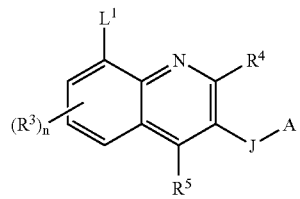

(II)

with a compound of formula (III)

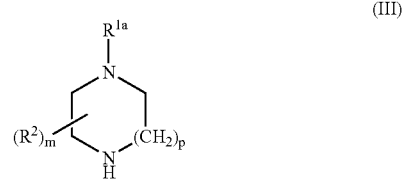

(III)

wherein $R^{1a}$ is as defined for $R^1$ or an N-protecting group, $R^2$, $R^3$, $R^4$, $R^5$, m, n, p, J and A are as defined above and $L^1$ represents a suitable leaving group, such as a halogen atom (e.g. a bromine or iodine atom) or a trifluoromethylsulfonyloxy group, and thereafter as necessary removing an $R^{1a}$ N-protecting group. The N-protecting group used may be any conventional group e.g. t-butyloxycarbonyl (Boc) or benzyloxycarbonyl. Further N-protecting groups which may be used include methyl.

(b) deprotecting a compound of formula (I) which is protected; and thereafter optionally (c) interconversion to other compounds of formula (I) and/or forming a pharmaceutically acceptable salt and/or solvate.

Process (a) may be performed in the presence of a palladium, nickel or copper catalyst, for example a mixture of a palladium source such as $Pd_2(dba)_3$ and a suitable ligand such as (R)-, (S)- or (+)-2,2'-bis(diphenylphosphino)-1,1'-binaphthyl (BINAP) or (2-dicyclohexylphosphanylphenyl-dimethylamine, or 1,1'-bis-diphenylphosphinoferrocene together with a suitable base such as sodium t-butoxide, in an inert solvent such as 1,4-dioxane. The process typically requires elevated temperature and may advantageously be carried out using a microwave oven.

In processes (a) and (b), examples of protecting groups and the means for their removal can be found in T. W. Greene 'Protective Groups in Organic Synthesis' (J. Wiley and Sons, 1991). Suitable amine protecting groups include sulfonyl (e.g. tosyl), acyl (e.g. acetyl, 2',2',2'-trichloroethoxycarbonyl, benzyloxycarbonyl or t-butoxycarbonyl) and arylalkyl (e.g. benzyl), which may be removed by hydrolysis (e.g. using an acid such as hydrochloric acid) or reductively (e.g. hydrogenolysis of a benzyl group or reductive removal of a 2',2',2'-trichloroethoxycarbonyl group using zinc in acetic acid) as appropriate. Other suitable amine protecting groups include trifluoroacetyl (—$COCF_3$) which may be removed by base catalysed hydrolysis or a solid phase resin bound benzyl group, such as a Merrifield resin bound 2,6-dimethoxybenzyl group (Ellman linker), which may be removed by acid catalysed hydrolysis, for example with trifluoroacetic acid. A further amine protecting group includes methyl which may be removed using standard methods for N-dealkylation (e.g. 1-chloroethyl chloroformate under basic conditions followed by treatment with methanol).

Process (c) may be performed using conventional interconversion procedures such as epimerisation, oxidation, reduction, reductive alkylation, alkylation, nucleophilic or electrophilic aromatic substitution, ester hydrolysis or amide bond formation. For example, N-dealkylation of a compound of formula (I) wherein $R^1$ represents an alkyl group to give a compound of formula (I) wherein $R^1$ represents hydrogen, or reduction of a compound of formula (I) where J represents a CO group to give a compound of formula (I) where J represents $CH_2$ or CH(OH). It will be appreciated that such interconversion may be interconversion of protected derivatives of formula (I) which may subsequently be deprotected following interconversion.

In addition, process (c) may comprise, for example, reacting a compound of formula (I), wherein $R^1$ represents hydrogen, with an appropriate aldehyde or ketone in the presence of a reducing agent in order to generate a compound of formula (I) where $R^1$ represents other than hydrogen. This may be performed using a hydride donor agent such as sodium cyanoborohydride, sodium triacetoxyborohydride or a resin bound form of cyanoborohydride in an alcoholic solvent such as ethanol and in the presence of an acid such as acetic acid, or under conditions of catalytic hydrogenation. Alternatively, such a transformation may be carried out by reacting a compound of formula (I), wherein $R^1$ represents hydrogen, with a compound of formula $R^1$-L, wherein $R^1$ is as defined above and L represents a leaving group such as a halogen atom (e.g. bromine or iodine) or methylsulfonyloxy group, optionally in the presence of a suitable base such as potassium carbonate or triethylamine using an appropriate solvent such as N,N-dimethylformamide or a $C_{1-4}$alkanol.

Compounds of formula (II) wherein J represents O may be prepared by reaction of a compound of formula (IV)

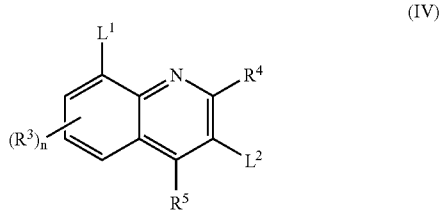

(IV)

wherein $R^3$, $R^4$, $R^5$, n, and $L^1$ are as defined above and $L^2$ represents a leaving group such as iodo or trifluoromethylsulfonyl, with a compound of formula A-OH wherein A is as defined above, in the presence of a suitable metal salt. Such a reaction may be advantageously carried out in the presence of a copper (I) salt such as copper (I) phenylacetylide, optionally using an excess of the compound of formula A-OH, in a suitable solvent such as pyridine at elevated temperature, e.g. at reflux temperature.

Compounds of formula (II) wherein J represents $CH_2$ may be prepared by reaction of a compound of formula $(IV)^a$

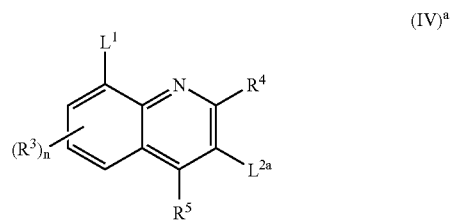

$(IV)^a$ wherein $R^3$, $R^4$, $R^5$, n, and $L^1$ are as defined above and $L^{2a}$ represents a halogen atom such as bromine or preferably iodine, with an alkyl magnesium halide (e.g. isopropylmagnesium chloride) in a suitable solvent such as tetrahydrofuran, followed by quenching of the resulting 3-quinolinylmagnesium halide with a compound of formula A-CHO where A is as defined above, and subsequent reduction with a suitable reducing agent such as iodotrimethylsilane in an appropriate solvent such as acetonitrile. For the final reduction step, the iodotrimethylsilane may be optionally generated in situ from chlorotrimethylsilane and an iodide source such as sodium iodide, and the reaction may be carried out at elevated temperature, e.g. 150° C., optionally using microwave irradiation.

Compounds of formula (II) wherein J represents CO may be prepared by reaction of a compound of formula $(IV)^a$, as defined above, with an alkyl magnesium halide (e.g. isopropylmagnesium chloride) in a suitable solvent such as tetrahydrofuran, followed by reaction of the resulting 3-quinolinylmagnesium halide with a compound of formula A-C(=O)$L^3$ where A is as defined above and $L^3$ represents a leaving group such as halogen (e.g. a chlorine atom) or N-methyl-O-methylhydroxyamino. Where $L^3$ represents a chlorine atom, the reaction may be advantageously performed by treatment of the 3-quinolinylmagnesium halide with a suitable metal salt such as copper (I) cyanide prior to addition of the compound of formula A-C(=O)$L^3$. Such a process is typically carried out below ambient temperature, e.g. −40° C.

Compounds of formula (II) wherein J represents S may be prepared by reaction of a compound of formula (IV), as defined above, with a compound of formula A-SH, wherein A is as defined above, in the presence of a base such as sodium hydride or potassium phosphate in a suitable solvent such as anhydrous N,N-dimethylformamide or ethylene glycol, advantageously in the presence of a copper (I) salt as catalyst, for example copper (I) iodide or copper (I) trifluoromethylsulfonate benzene complex.

Compounds of formula (II) wherein J represents SO may be prepared by reaction of a compound of formula (IV), as defined above, with a compound of formula A-SH in the manner described above, followed by treatment of the resulting thioether with a suitable oxidising agent such as monomagnesium peroxyphthalate, 3-chloroperbenzoic acid, peracetic acid or potassium monopersulfate.

Compounds of formula (IV) where $L^2$ represents halogen and compounds of formula $(IV)^a$ may be prepared by reaction of a compound of formula (V)

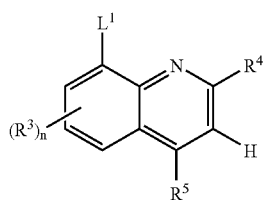

(V)

wherein $R^3$, $R^4$, $R^5$, n, and $L^1$ are as defined above with an appropriate halogenating reagent, for example when $L^2$ or $L^{2a}$ represents an iodine atom an appropriate process comprises reaction of compound (V) with N-iodosuccinimide in the presence of acetic acid at elevated temperature, e.g. 80° C. Such a reaction may be advantageously carried out using acetic acid as solvent.

Compounds of formula (III) and (V) are known in the literature or can be prepared by analogous methods.

Pharmaceutically acceptable salts may be prepared conventionally by reaction with the appropriate acid or acid derivative.

Compounds of formula (I) and their pharmaceutically acceptable salts have affinity for the $5HT_6$ receptor and are believed to be of potential use in the treatment of certain CNS disorders such as anxiety, depression, epilepsy, obsessive compulsive disorders, migraine, cognitive memory disorders (e.g. Alzheimer's disease, age related cognitive decline and mild cognitive impairment), Parkinson's Disease, ADHD (Attention Deficit Disorder/Hyperactivity Syndrome), sleep disorders (including disturbances of Circadian rhythm), feeding disorders such as anorexia and bulimia, panic attacks, withdrawal from drug abuse such as cocaine, ethanol, nicotine and benzodiazepines, schizophrenia (in particular cognitive deficits of schizophrenia), stroke and also disorders associated with spinal trauma and/or head injury such as hydrocephalus. Compounds of the invention are also expected to be of use in the treatment of certain GI (gastrointestinal) disorders such as IBS (irritable Bowel Syndrome). Compounds of the invention are also expected to be of use in the treatment of obesity.

Thus the invention also provides a compound of formula (I) or a pharmaceutically acceptable salt thereof, for use as a therapeutic substance, in particular in the treatment or prophylaxis of the above disorders. In particular the invention provides for a compound of formula (I) or a pharmaceutically acceptable salt thereof, for use in the treatment of depression, anxiety, Alzheimer's disease, age related cognitive decline, ADHD, obesity, mild cognitive impairment, schizophrenia, cognitive deficits in schizophrenia and stroke.

The invention further provides a method of treatment or prophylaxis of the above disorders, in mammals including humans, which comprises administering to the sufferer a therapeutically effective amount of a compound of formula (I) or a pharmaceutically acceptable salt thereof.

In another aspect, the invention provides the use of a compound of formula (I) or a pharmaceutically acceptable salt thereof in the manufacture of a medicament for use in the treatment or prophylaxis of the above disorders.

$5-HT_6$ antagonists have the potential to be capable of increasing basal and learning-induced polysialylated neuron cell frequency in brain regions such as the rat medial temporal lobe and associated hippocampus, as described in WO 03/066056. Thus, according to a further aspect of the present invention, we provide a method of promoting neuronal growth within the central nervous system of a mammal which comprises the step of administering a compound of formula (I) or a pharmaceutically acceptable salt thereof.

In order to use the compounds of formula (I) in therapy, they will normally be formulated into a pharmaceutical composition in accordance with standard pharmaceutical practice. The present invention also provides a pharmaceutical composition, which comprises a compound of formula (I) or a pharmaceutically acceptable salt thereof, and a pharmaceutically acceptable carrier.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusable solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colourants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 0.05 to 200 mg, for example 20 to 40 mg; and such unit doses will preferably be administered once a day, although administration more than once a day may be required; and such therapy may extend for a number of weeks or months.

All publications, including but not limited to patents and patent applications, cited in this specification are herein incorporated by reference as if each individual publication were specifically and individually indicated to be incorporated by reference herein as though fully set forth.

The following Descriptions and Examples illustrate the preparation of compounds of the invention.

DESCRIPTION 1

8-Chloro-3-iodoquinoline (D1)

N-Iodosuccinimide (67.9 g, 0.30 mmol) was added in portions to a stirred solution of 8-chloroquinoline (49 g, 0.30 mmol) (*J. Org. Chem.*, 1987, 52, 1673-80) in acetic acid (300 ml) at 70° C. under argon. The mixture was heated to 70° C. for 18 h and then concentrated in vacuo. The residue was redissolved in dichloromethane (600 ml) and the solution was washed successively with 10% aqueous sodium thiosulfate solution (2×300 ml) and 10% aqueous sodium hydrogen carbonate solution (2×300 ml), dried (MgSO$_4$) and concentrated in vacuo to a solid. The solid was recrystallised from ethyl acetate to afford the title compound (D1) as a yellow solid (42 g, 0.145 mol, 48%). The residue from recrystallisation was purified by chromatography over silica gel eluting with a toluene/acetone gradient to afford a second crop of the product (18 g, total yield 69%).

$\delta_H$(CDCl$_3$) 7.49 (1H, t, J=8.1 Hz), 7.65 (1H, dd, J=1.4 Hz, 8.3 Hz), 7.85 (1H, dd, J=1.3 Hz, 7.4 Hz), 8.57 (1H, d, J=2.1 Hz), 9.15 (1H, d, J=2.1 Hz).

Mass Spectrum: C$_9$H$_5$ClIN requires 289, 291; found 290, 292 (MH$^+$)

DESCRIPTION 2

(3-Chlorophenyl)(8-chloro-3-quinolinyl)methanol (D2)

iso-Propyl magnesium chloride (2M solution in tetrahydrofuran)(3.76 ml, 7.5 mmol) was added dropwise over 0.25 h to a stirred solution of 8-chloro-3-iodoquinoline (D1)(2.0 g, 6.9 mmol) in tetrahydrofuran (16 ml) at −40° C. under argon. After stirring the solution at this temperature for 0.5 h, 3-chlorobenzaldehyde (0.77 ml, 6.8 mmol) was added dropwise over 10 mins. The solution was allowed to warm to ambient temperature over 1 h and then quenched by the addition of a saturated solution of sodium chloride (100 ml). The mixture was extracted with ethyl acetate (2×100 ml). The combined extracts were dried (MgSO$_4$) and concentrated in vacuo to give the title compound (D2) as a crude solid (1.84 g, 6.0 mmol, 88%) which was used directly in the next stage (see D3).

$\delta_H$(CDCl$_3$) 2.54 (1H, d, J=3.5 Hz), 6.06 (1H, d, J=3.4 Hz), 7.29 (3H, br, s), 7.43-7.51 (2H, m), 7.76 (1H, dd, J=1.3 Hz, 8.2 Hz), 7.83 (1H, dd, J=1.3 Hz, 7.5 Hz), 8.20 (1H, d, J=1.6 Hz), 8.99 (1H, d, J=1.6 Hz).

Mass Spectrum: C$_{16}$H$_{11}$Cl$_2$NO requires 303, 305; found 304, 306 (MH$^+$)

DESCRIPTION 3

8-Chloro-3-[(3-chlorophenyl)methyl]quinoline (D3)

A stirred suspension of (3-chlorophenyl)(8-chloro-3-quinolinyl)methanol (D2)(1.4 g, 4.6 mmol), trimethylsilyl chloride (3.5 ml, 28 mmol) and sodium iodide (4.2 g, 28 mmol) in acetonitrile (28 ml) was heated in a sealed tube in a microwave oven at 150° C. for 35 mins. The mixture was filtered and the solid washed with dichloromethane (5 ml) and diethyl ether (5 ml). The filtrate and washings were concentrated in vacuo to a dark brown solid, which was redissolved in dichloromethane (75 ml) and the solution washed with 10% aqueous sodium sulfite solution (75 ml), dried (MgSO$_4$) and concentrated in vacuo to an oil. The oil was purified by chromatography over silica gel eluting with a gradient of acetone/toluene to give the title compound (D3) as a pale yellow solid (1.04 g, 3.6 mmol, 78%).

$\delta_H$(CDCl$_3$) 7.49 (1H, t, J=8.1 Hz), 7.65 (1H, dd, J=1.4 Hz, 8.3 Hz), 7.85 (1H, dd, J=1.3 Hz, 7.4 Hz), 8.57 (1H, d, J=2.1 Hz), 9.15 (1H, d, J=2.1 Hz).

Mass Spectrum: C$_{16}$H$_{11}$Cl$_2$N requires 287, 289; found 288, 290 (MH$^+$)

DESCRIPTION 4

1,1-Dimethylethyl 4-{3-[(3-chlorophenyl)methyl]-8-quinolinyl}-1-piperazinecarboxylate (D4)

A stirred suspension of 8-chloro-3-[(3-chlorophenyl)methyl]quinoline (D3)(0.25 g, 0.87 mmol), 1,1-dimethylethyl 1-piperazinecarboxylate (0.228 g, 1.2 mmol), tris(dibenzylideneacetone)dipalladium (0) (0.025 g, 0.027 mmol), 2-dicyclohexylphosphino-2'-(N,N-dimethylamino)biphenyl (0.03 g, 0.076 mmol) and sodium tert-butoxide (0.118 g, 1.23 mmol) in degassed 1,4-dioxan (3.8 ml) under argon was heated at 80° C. under argon of 18 h. The cooled reaction mixture was diluted with dichloromethane (50 ml) and washed with water (50 ml), dried (MgSO$_4$) and concentrated in vacuo to an oil. The oil was purified by chromatography over silica gel eluting with a gradient of acetone/toluene to give the title compound (D4) as an oil (0.202 g, 0.46 mmol, 53%).

$\delta_H$(CDCl$_3$) 1.50 (9H, s), 3.31-3.36 (4H, m), 3.73-3.77 (4H, m), 4.12 (2H, s), 7.06-7.12 (2H, m), 7.20-7.27 (3H, m), 7.37-7.46 (2H, m), 7.85 (1H, d, J=2.3 Hz), 8.75 (1 H, d, J=2.3 Hz).

Mass Spectrum: C$_{25}$H$_{28}$ClN$_3$O$_2$ requires 437, 439; found 438, 440 (MH$^+$)

DESCRIPTION 5

(3-Chlorophenyl)(8-chloro-3-quinolinyl)methanone (D5)

iso-Propyl magnesium chloride (2M solution in tetrahydrofuran) (2.85 ml, 5.7 mmol) was added dropwise over 5 mins to a stirred solution of 8-chloro-3-iodoquinoline (D1) (1.5 g, 5.2 mmol) in tetrahydrofuran (15 ml) at −40° C. under argon. After stirring the solution at this temperature for 0.3 h, copper (I) cyanide (0.47 g, 5.2 mmol) was added in portions over 5 mins. The whole mixture was left to stir at −40° C. for a further 10 mins and then 3-chlorobenzoyl chloride (1.0 g, 5.7 mmol) was added dropwise over 10 mins. The temperature was maintained at −40° C. for 0.5 h and then the reaction was warmed to 0° C. at which temperature it was quenched by the addition of a saturated solution of sodium chloride (100 ml). The mixture was extracted with ethyl acetate (2×50 ml). The combined extracts were dried (MgSO$_4$) and concentrated in vacuo to a solid. The solid was purified by chromatography over silica gel eluting with a gradient of acetone/toluene to give the title compound (D5) as a white solid (0.95 g, 3.1 mmol, 60%).

δ$_H$ (CDCl$_3$) 7.52 (1H, t, J=7.8 Hz), 7.60-7.75 (3H, m), 7.85-7.91 (2H, m), 8.00 (1H, dd, J=1.3 Hz, 7.5 Hz), 8.60 (1H, d, J=2.1 Hz), 9.40 (1H, d, J=2.1 Hz).

Mass Spectrum: C$_{16}$H$_9$Cl$_2$NO requires 301, 303; found 302, 304 (MH$^+$)

DESCRIPTION 6

1,1-Dimethylethyl 4-{3-[(3-chlorophenyl)carbonyl]-8-quinolinyl}-1-piperazinecarboxylate (D6)

A stirred suspension of (3-chlorophenyl)(8-chloro-3-quinolinyl)methanone (D5)(0.63 g, 2.1 mmol), 1,1-dimethylethyl 1-piperazinecarboxylate (0.43 g, 2.3 mmol), tris (dibenzylideneacetone)dipalladium (0) (0.058 g, 0.064 mmol), 2-dicyclohexylphosphino-2'-(N,N-dimethylamino) biphenyl (0.074 g, 0.19 mmol) and sodium tert-butoxide (0.22 g, 2.3 mmol) in degassed toluene (3.5 ml) was heated in a sealed tube at 150° C. for 10 mins in a microwave oven. The cooled reaction mixture was washed with water (20 ml), dried (MgSO$_4$) and concentrated in vacuo to an oil. The oil was purified by chromatography over silica gel eluting with a gradient of ethyl acetate/hexane to afford the title compound (D6) as a yellow foam (0.37 g, 0.81 mmol, 39%).

δ$_H$(CDCl$_3$) 1.51 (9H, s), 3.36-3.40 (4H, m), 3.76-3.80 (4H, m), 7.49 (1H, t, J=7.8 Hz), 7.55-7.66 (4H, m), 7.71-7.76 (1H, m), 7.84-7.86 (1H, m), 8.54 (1H, d, J=2.3 Hz), 9.24 (1H, d, J=2.3 Hz).

Mass Spectrum: C$_{25}$H$_{26}$ClN$_3$O$_3$ requires 451, 453; found 452, 454 (MH$^+$)

DESCRIPTION 7

8-Chloro-3-(phenyloxy)quinoline (D7)

A stirred suspension of phenol (0.35 g, 3.7 mmol) and copper (I) phenylacetylide (0.306 g, 1.9 mmol) in dry pyridine (8 ml) was heated at reflux for 18 h under argon. 8-Chloro-3-iodoquinoline (D1)(0.55 g, 1.9 mmol) was then added and the mixture was further refluxed for 18 h. The reaction mixture was concentrated in vacuo to an oily residue which was re-evaporated with toluene (2×50 ml). The resulting gum was dissolved in dichloromethane (50 ml) and the solution washed with 0.5M aqueous sodium hydroxide (50 ml), dried (MgSO$_4$) and concentrated in vacuo to an oil. The oil was purified by chromatography over silica gel eluting with a gradient of ethyl acetate/hexane to afford an oil (0.19 g) with Rf 0.35 (tlc eluant, ethyl acetate:hexane 1:9). This oil was stirred with diethyl ether/hexane (1:1)(3 ml) to give an unwanted solid which was removed by filtration. The filtrate was concentrated in vacuo to give the title compound (D7) as an oil (0.12 g, 0.47 mmol, 25%).

δ$_H$ (CDCl$_3$) 7.10-7.26 (3H, m), 7.39-7.51 (4H, m), 7.58 (1H, dd, J=1.3 Hz, 8.3 Hz), 7.73 (1H, dd, J=1.3 Hz, 7.4 Hz), 8.92 (1H, d, J=2.7 Hz).

Mass Spectrum: C$_{15}$H$_{10}$ClNO requires 255, 257; found 256, 258 (MH$^+$)

DESCRIPTION 8

1,1-Dimethylethyl 4-[3-(phenyloxy)-8-quinolinyl]-1-piperazinecarboxylate (D8)

A stirred suspension of 8-chloro-3-(phenyloxy)quinoline (D7)(0.115 g, 0.45 mmol), 1,1-dimethylethyl 1-piperazinecarboxylate (0.084 g, 0.45 mmol), tris(dibenzylideneacetone)dipalladium (0) (0.012 g, 0.014 mmol), 2-dicyclohexylphosphino-2'-(N,N-dimethylamino)biphenyl (0.016 g, 0.041 mmol) and sodium tert-butoxide (0.043 g, 0.45 mmol) in degassed toluene (2.5 ml) was heated in a sealed tube at 150° C. for 10 mins in a microwave oven. The cooled reaction mixture was washed with water (20 ml), dried (MgSO$_4$) and concentrated in vacuo to an oil. The oil was purified by chromatography over silica gel eluting with a gradient of ethyl acetate/hexane to afford the title compound (D8) as a yellow oil (0.09 g, 0.22 mmol, 49%).

δ$_H$(CDCl$_3$) 1.50 (9H, s), 3.33-3.36 (4H, m), 3.74-3.78 (4H, m), 7.02-7.45 (8H, m), 7.51 (1H, d, J=2.8 Hz), 8.74 (1H, d, J=2.8 Hz).

Mass Spectrum: C$_{24}$H$_{27}$N$_3$O$_3$ requires 405; found 406 (MH$^+$)

EXAMPLE 1

3-[(3-Chlorophenyl)methyl]-8-(1-piperazinyl)quinoline hydrochloride (E1)

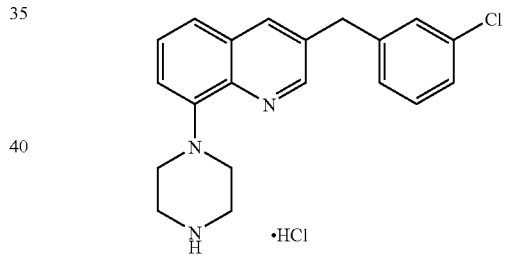

A stirred solution of 1,1-dimethylethyl 4-{3-[(3-chlorophenyl)methyl]-8-quinolinyl}-1-piperazinecarboxylate (D4) (0.25 g, 0.57 mmol) in 1,4-dioxan (2.5 ml) and aqueous 4 M hydrochloric acid (2.5 ml) was heated at 70° C. for 3 h under argon. The reaction mixture was concentrated in vacuo and the residue was dissolved in 0.2M aqueous sodium hydroxide solution (15 ml) and extracted with dichloromethane (2×15 ml). The combined organic extracts were dried (MgSO$_4$) and concentrated in vacuo to an oil. The oil was purified by chromatography over silica gel eluting with a gradient of dichloromethane/methanol/ammonium hydroxide (sg=0.88) to afford the corresponding free base (0.1 g) of the title compound (E1). Treatment of a solution of this material in acetone with 1M hydrogen chloride in diethyl ether gave the title compound (E1)(0.085 g, 0.23 mmol, 40%).

δ$_H$(d$_6$-DMSO) 3.36 (4H, br, s), 3.43 (4H, br, s), 4.21 (2H, s), 7.24-7.41 (5H, m), 7.53-7.67 (2H, m), 8.38 (1H, br, s), 8.88 (1H, d, J=2.1 Hz), 9.11 (2H, br, s).

Mass Spectrum: C$_{20}$H$_{20}$ClN$_3$ requires 337, 339; found 338, 340 (MH$^+$)

EXAMPLE 2

(3-Chlorophenyl)[8-(1-piperazinyl)-3-quinolinyl]methanone hydrochloride (E2)

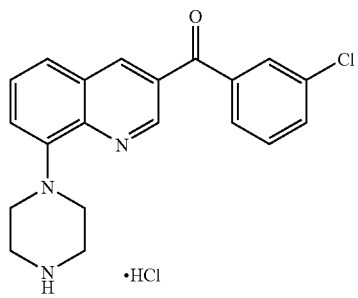

A stirred solution of 1,1 dimethylethyl 4-{3-[(3-chlorophenyl)carbonyl]-8-quinolinyl}-1-piperazinecarboxylate (D6) (0.15 g, 0.33 mmol) in 1,4-dioxan (3 ml) and aqueous 4 M hydrochloric acid (3 ml) was heated at 80° C. for 1.5 h under argon. The reaction mixture was concentrated in vacuo and the residue was stirred with acetone/diethyl ether (2:1)(10 ml) to afford the title compound (E2) as a yellow solid (0.126 g, 0.32 mmol, 98%).

$\delta_H$ (d$_6$-DMSO) 3.37 (4H, br, s), 3.60 (4H, br, s), 7.41 (1H, d, J=7.6 Hz), 7.60-7.68 (2H, m), 7.79-7.87 (4H, m), 8.75 (1H, d, J=2.2 Hz), 9.14 (1H, d, J=2.2Hz), 9.21 (2H, br, s).

Mass Spectrum: $C_{20}H_{18}ClN_3O$ requires 351, 353; found 352, 354 (MH$^+$)

EXAMPLE 3

3-(Phenyloxy)-8-(1-piperazinyl)quinoline hydrochloride (E3)

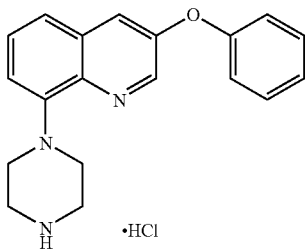

A stirred solution of 1,1-dimethylethyl 4-[3-(phenyloxy)-8-quinolinyl]-1-piperazinecarboxylate (D8) (0.085 g, 0.21 mmol) in 1,4-dioxan (2 ml) and aqueous 4 M hydrochloric acid (2 ml) was heated at 80° C. for 2 h under argon. The reaction mixture was concentrated in vacuo to a residue which was re-evaporated with toluene (2×50 ml) to yield the title compound as a foam (0.075 g, 0.22 mmol, 100%).

$\delta_H$ (d$_6$-DMSO) 3.36 (4H, br, s), 3.55 (4H, br, s), 7.17-7.27 (4H, m), 7.44-7.69 (4H, m), 7.88 (1H, d, J=2.8 Hz), 8.79 (1H, d, J=2.8 Hz), 9.44 (2H, br,s).

Mass Spectrum: $C_{19}H_{19}N_3O$ requires 305; found 306 (MH$^+$)

PHARMACOLOGICAL DATA

Compounds can be tested following the procedures outlined in WO98/27081. The compounds of Examples E1-E3 were tested and showed affinity for the 5-HT$_6$ receptor, having pKi values>6.0 at human cloned 5-HT$_6$ receptors. More particularly, the compounds of Examples E1-E2 exhibited pKi values>7.5.

What is claimed is:

1. A compound of formula (I):

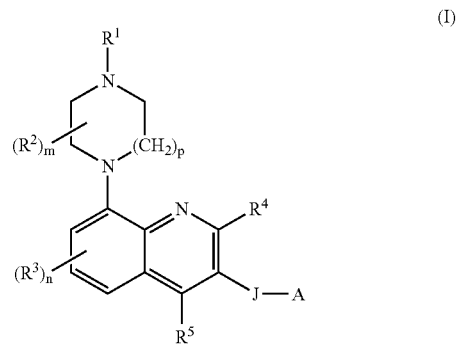

wherein:
R$^1$ represents hydrogen or methyl;
R$^2$ represents hydrogen or methyl;
m represents 1;
R$^3$ represents hydrogen, methyl or halogen;
R$^4$ and R$^5$ independently represent hydrogen or methyl;
n represents 1;
p represents 1 or 2;
J represents CH$_2$, CO, or O;
A represents phenyl optionally substituted by a halogen atom;
or a pharmaceutically acceptable salt thereof, or a hydrate thereof.

2. A compound which is:
3-[(3-Chlorophenyl)methyl]-8-(1-piperazinyl)quinoline;
(3-Chlorophenyl)[8-(1-piperazinyl)-3-quinolinyl]methanone;
3-(Phenyloxy)-8-(1-piperazinyl)quinoline;
or a pharmaceutically acceptable salt thereof, or a hydrate thereof.

3. A pharmaceutical composition which comprises the compound, salt, or hydrate according to claim 1 and a pharmaceutically acceptable carrier or excipient.

4. A pharmaceutical composition which comprises the compound, salt, or hydrate according to claim 2 and a pharmaceutically acceptable carrier or excipient.

5. A method of treating a cognitive memory disorder which comprises administering a therapeutically effective amount of the compound, salt, or hydrate according to claim 1 to a patient in need thereof, wherein the cognitive memory disorder is selected from age related cognitive decline, mild cognitive impairment, and cognitive deficits in schizophrenia.

6. A method of treating a cognitive memory disorder which comprises administering a therapeutically effective amount of the compound, salt, or hydrate according to claim 2 to a patient in need thereof, wherein the cognitive memory disorder is selected from age related cognitive decline, mild cognitive impairment, and cognitive deficits in schizophrenia.

7. A method of treating depression or anxiety which comprises administering to a patient in need thereof a therapeutically effective amount of the compound, salt, or hydrate according to claim 1.

8. A method of treating depression or anxiety which comprises administering to a patient in need thereof a therapeutically effective amount of the compound, salt, or hydrate according to claim 2.

9. A method of treating obesity which comprises administering to a patient in need thereof a therapeutically effective amount of the compound, salt, or hydrate according to claim 1.

10. A method of treating obesity which comprises administering to a patient in need thereof a therapeutically effective amount of the compound, salt, or hydrate according to claim 2.

11. A method of treating Alzheimers disease which comprises administering to a patient in need thereof a therapeutically effective amount of the compound, salt, or hydrate according to claim 1.

12. A method of treating Alzheimers disease which comprises administering to a patient in need thereof a therapeutically effective amount of the compound, salt, or hydrate according to claim 2.

* * * * *